US009795449B2

(12) United States Patent
Baldwin

(10) Patent No.: US 9,795,449 B2
(45) Date of Patent: Oct. 24, 2017

(54) METHODS AND DEVICES FOR PERFORMING ABDOMINAL SURGERY

(71) Applicant: FACULTY PHYSICIANS AND SURGEONS OF LOMA LINDA UNIVERSITY SCHOOL OF MEDICINE, Loma Linda, CA (US)

(72) Inventor: Dalton Duane Baldwin, Loma Linda, CA (US)

(73) Assignee: FACULTY PHYSICIANS AND SURGEONS OF LOMA LINDA UNIVERSITY SCHOOL OF MEDICINE, Loma Linda, CA (US)

( * ) Notice: Subject to any disclaimer, the term of this patent is extended or adjusted under 35 U.S.C. 154(b) by 157 days.

(21) Appl. No.: 14/614,213

(22) Filed: Feb. 4, 2015

(65) Prior Publication Data

US 2015/0216605 A1  Aug. 6, 2015

Related U.S. Application Data

(60) Provisional application No. 61/936,548, filed on Feb. 6, 2014.

(51) Int. Cl.
*A61B 19/00* (2006.01)
*A61B 17/00* (2006.01)
(Continued)

(52) U.S. Cl.
CPC .......... *A61B 19/2203* (2013.01); *A61B 34/30* (2016.02); *A61B 34/71* (2016.02);
(Continued)

(58) Field of Classification Search
CPC ................ A61B 19/2203; A61B 34/30; A61B 2034/305; A61B 2017/00477; A61B 34/71; Y10T 29/49826
See application file for complete search history.

(56) References Cited

U.S. PATENT DOCUMENTS 5,441,059 A    8/1995  Dannan
5,792,165 A *  8/1998  Klieman ............... A61B 17/29
                                                 606/170
(Continued)

FOREIGN PATENT DOCUMENTS

CA    2762552      11/2011
EP    2 432 372    3/2012
(Continued)

OTHER PUBLICATIONS

International Search Report and Written Opinion, re PCT App. No. PCT/US2015/014501, dated May 13, 2015.

*Primary Examiner* — Catherine Voorhees
(74) *Attorney, Agent, or Firm* — Knobbe Martens Olson & Bear LLP

(57) ABSTRACT

A surgical instrument and methods of use. The surgical instrument can include a control portion having a plurality of tubular shaft portions and a plurality of control rods. Each of the plurality of tubular shaft portions can have a diameter of less than or equal to about 2.5 mm. At least one of the plurality of control rods can extend through each of the plurality of shaft portions. The surgical instrument can also include a tool portion having a plurality of tool rods and a plurality of tool cables. Each of the plurality of tool cables can be connected to one of the plurality of control rods. Further, each of the tool rods can be removably connected to one of the plurality of control rods.

22 Claims, 11 Drawing Sheets

(51) Int. Cl.
*A61B 34/30* (2016.01)
*A61B 34/00* (2016.01)

(52) U.S. Cl.
CPC ............ *A61B 2017/00477* (2013.01); *A61B 2034/305* (2016.02); *Y10T 29/49826* (2015.01)

(56) References Cited

U.S. PATENT DOCUMENTS

| | | | |
|---|---|---|---|
| 5,855,583 A | 1/1999 | Wang et al. | |
| 6,309,397 B1 | 10/2001 | Julian et al. | |
| 7,666,181 B2 | 2/2010 | Abou El Kheir | |
| 7,927,327 B2* | 4/2011 | Lu | A61B 17/221 606/1 |
| 8,225,798 B2* | 7/2012 | Baldwin | A61B 17/29 128/898 |
| 8,721,539 B2 | 5/2014 | Shohat et al. | |
| 8,827,988 B2 | 9/2014 | Belson et al. | |
| 8,858,538 B2 | 10/2014 | Belson et al. | |
| 8,882,750 B2 | 11/2014 | Stefan et al. | |
| 2006/0079889 A1* | 4/2006 | Scott | A61B 17/3201 606/45 |
| 2006/0200186 A1 | 9/2006 | Marchek et al. | |
| 2008/0027279 A1 | 1/2008 | Abou El Kheir | |
| 2010/0179540 A1 | 7/2010 | Marczyk et al. | |
| 2010/0298774 A1 | 11/2010 | Igov | |
| 2011/0087267 A1 | 4/2011 | Spivey et al. | |
| 2011/0264136 A1 | 10/2011 | Choi et al. | |
| 2012/0083826 A1 | 4/2012 | Chao et al. | |
| 2012/0165611 A1 | 6/2012 | Warren et al. | |
| 2012/0203271 A1 | 8/2012 | Larkin et al. | |
| 2012/0259317 A1 | 10/2012 | Baldwin et al. | |
| 2013/0066304 A1 | 3/2013 | Belson et al. | |
| 2013/0096591 A1 | 4/2013 | Hart et al. | |
| 2014/0074135 A1* | 3/2014 | Hart | A61B 1/00087 606/170 |
| 2014/0200610 A1 | 7/2014 | Igov et al. | |
| 2014/0214027 A1 | 7/2014 | Smith et al. | |
| 2014/0336458 A1 | 11/2014 | Belson et al. | |

FOREIGN PATENT DOCUMENTS

| | | |
|---|---|---|
| WO | WO 2009/157719 | 12/2009 |
| WO | WO 2010/114634 | 10/2010 |
| WO | WO 2010/144219 | 12/2010 |
| WO | WO 2012/112622 | 8/2012 |
| WO | WO 2015/120080 | 8/2015 |

* cited by examiner

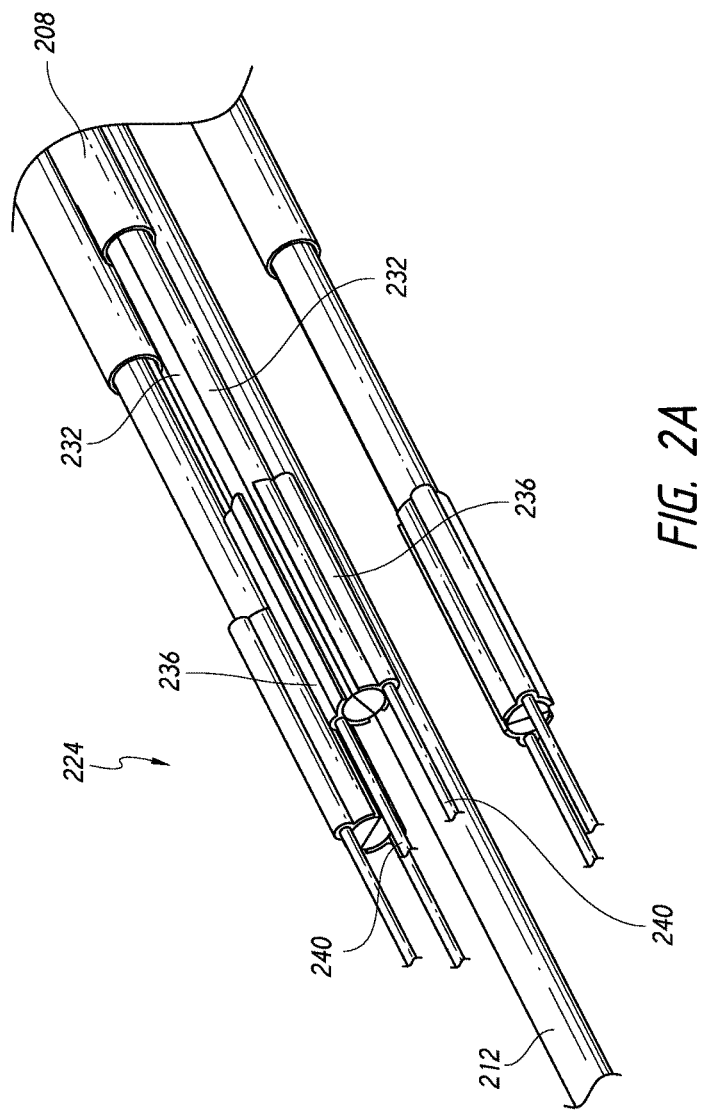

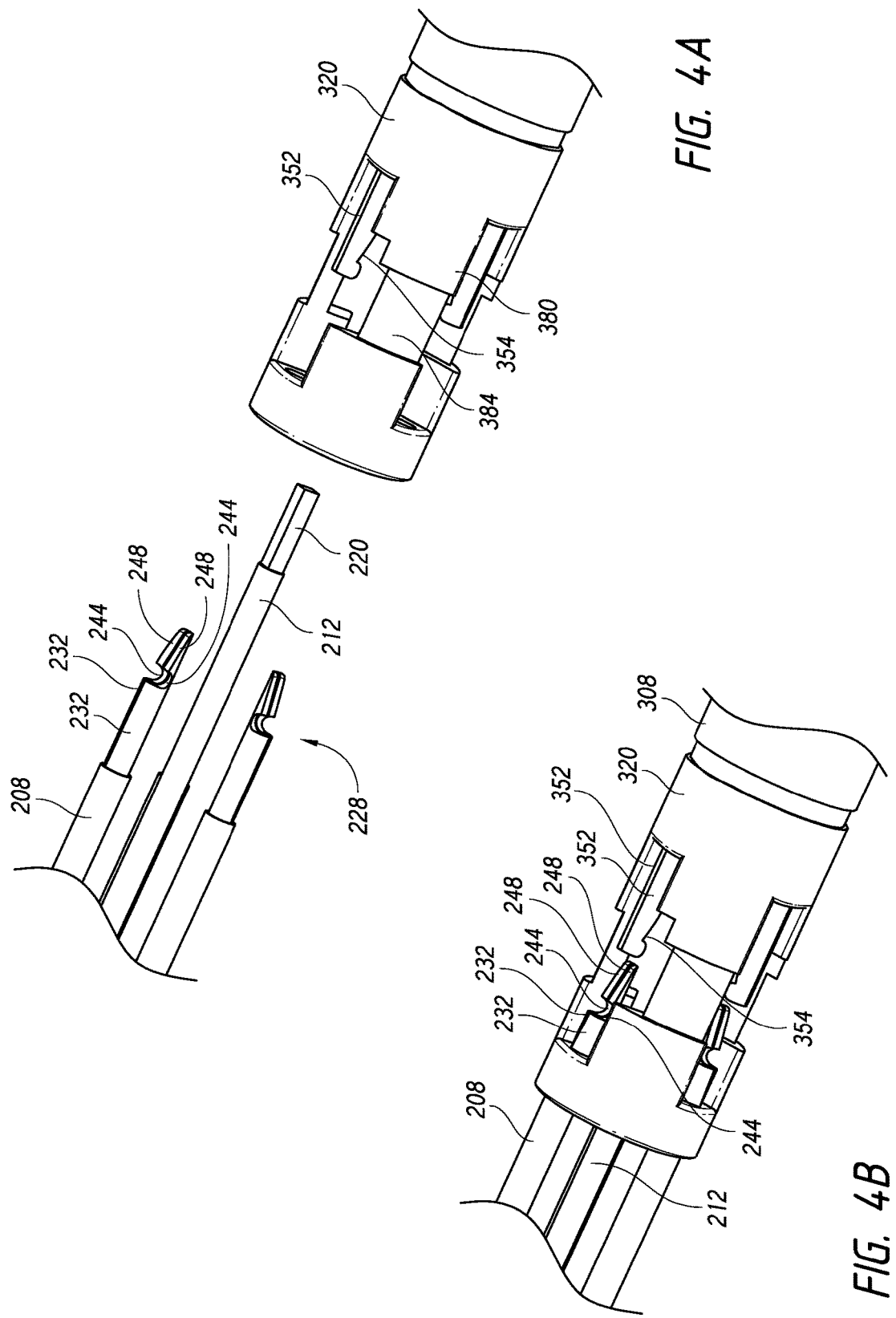

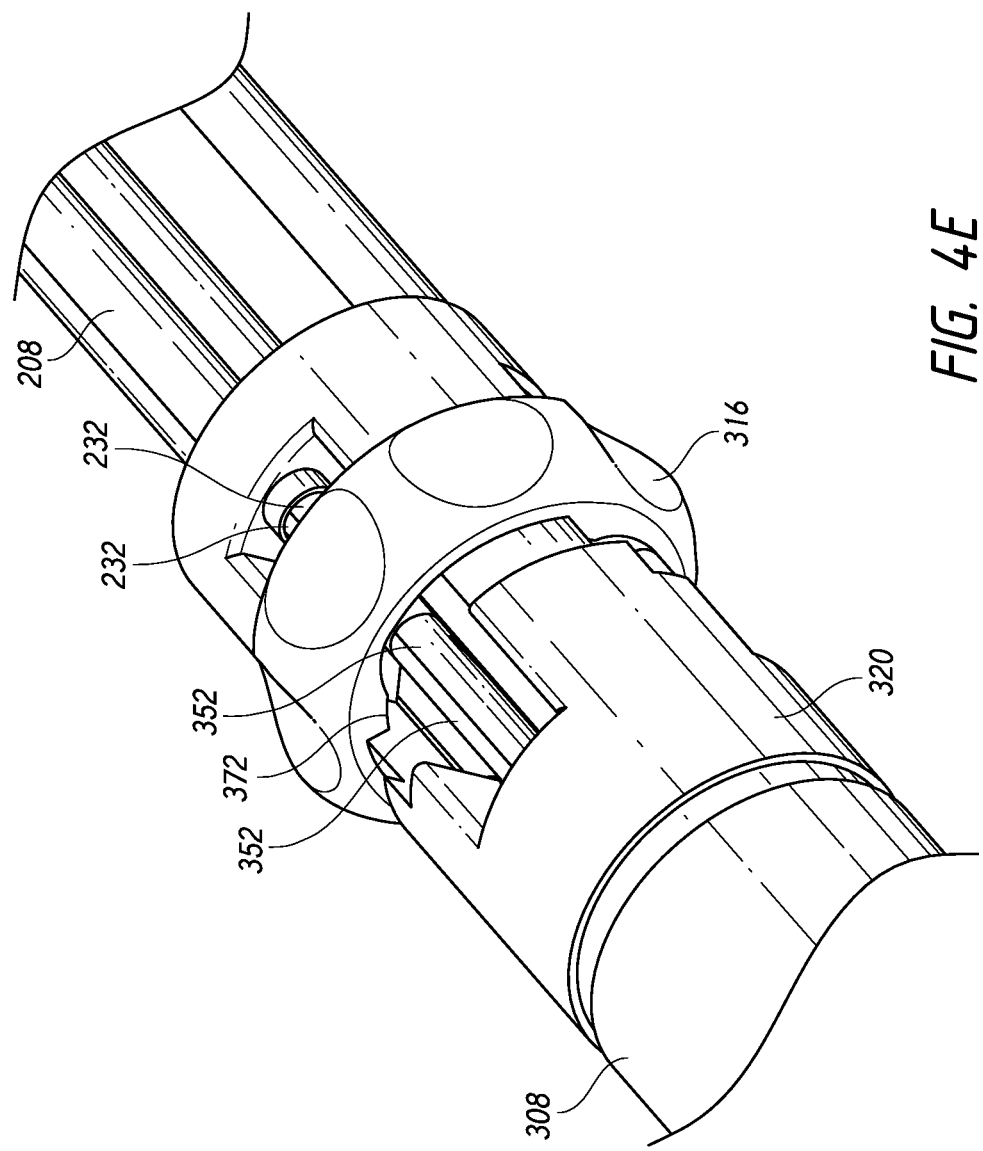

METHODS AND DEVICES FOR PERFORMING ABDOMINAL SURGERY

INCORPORATION BY REFERENCE TO ANY PRIORITY APPLICATIONS

The present application claims priority benefit under 35 U.S.C. §119(e) to U.S. Provisional Application No. 61/936,548, titled "METHODS AND DEVICES FOR PERFORMING SCARLESS, ROBOTIC ABDOMINAL SURGERY," filed Feb. 6, 2014.

Any and all applications for which a foreign or domestic priority claim is identified in the Application Data Sheet as filed with the present application, including without limitation the above-mentioned provisional application, are hereby incorporated by reference in their entirety under 37 C.F,R, §1.57 and for all purposes.

BACKGROUND

Field

The present disclosure relates to surgical devices and methods, including surgical devices used in scarless or robotic applications.

Description of the Related Art

Minimally invasive surgical tools are used to facilitate various abdominal surgical procedures. The surgical procedures can include creating one or more incisions that can accommodate different tools; however, certain known techniques for performing these surgeries can create scars.

SUMMARY

Certain aspects of the present disclosure are directed toward an instrument that can be used during surgery. The surgical instrument can include a control portion and a tool portion.

The control portion can include a plurality of tubular shaft portions and a plurality of control rods. The plurality of tubular shaft portions can each have an outer diameter of less than or equal to about 2.5 mm (e.g., less than or equal to about: 2.0 mm, 1.5 mm, 1.0 mm, or between about 1.0 mm and about 2.5 mm, or between about 1.0 mm and about 2.0 mm, or between about 1.5 mm and about 2.5 mm), such that the shaft portions can be inserted through incisions that leave behind no permanent scars. At least one of the plurality of control rods can extend through each of the plurality of shaft portions (e.g., one, two, three, or more control rods).

The tool portion can have a plurality of tool rods and a plurality of tool cables. Each of the plurality of tool cables can be secured to one of the plurality of tool rods (e.g., by a tool connector). Further, the tool portion can include the same number of tool rods as control rods. Each of the plurality of tool cables can removably connect to one of the plurality of control rods.

In the above-mentioned surgical instrument, the control portion can include an adapter that can engage a robotic arm. The adapter can include a plurality of control cables that can each be secured to one of the plurality of control rods (e.g., by a control connector).

In any of the above-mentioned surgical instruments, the tool portion can include a collapsible mandrel having an outer mandrel and an inner mandrel. Each of the plurality of tool cables can be secured to a proximal end of the collapsible mandrel and a distal end of the collapsible mandrel. In certain aspects, the outer mandrel can move relative to the inner mandrel along a cam path.

In any of the above-mentioned surgical instruments, the plurality of tool cables can drive a plurality of pulleys in a working end (e.g., scissors, forceps, electrocautery, or otherwise). For example, the plurality of pulleys can provide one or more of up-down working end movement, left-right working end movement, and operation of the tool (e.g., gripping, cutting, or otherwise).

In any of the above-mentioned surgical instruments, the control portion can include a central shaft surrounded by the plurality of tubular shaft portions. The central shaft can engage the collapsible mandrel. In certain aspects, the central shaft can rotate a working end of a tool and/or provide electrocautery capabilities.

In any of the above-mentioned surgical instruments, a distal portion of each of the control rods can include a control hook. Additionally, a proximal portion of each of the plurality of the tool rods can include a tool hook. Each control hook can removably engage one of the tool hooks.

In any of the above-mentioned surgical instruments, the tool portion can include a locking assembly for securing the plurality of the control rods with the plurality of tool rods. The locking assembly can include a frame member and a release ring surrounding the frame member. The release ring can have at least one cam surface that secures at least one of the plurality of control rods to at least one of the plurality of tool rods.

In any of the above-mentioned surgical instruments, the surgical instrument can include a support structure surrounding the plurality of shaft portions to maintain alignment of the plurality of shaft portions.

Certain aspects of the disclosure are directed toward a method of using any of the surgical instruments described above. The method can include forming a plurality of control incisions and a tool incision on a patient. Each of the control incisions can have a length of less than or equal to about 2.5 mm (e.g., less than or equal to about: 2.0 mm, 1.5 mm, 1.0 mm, or between about 1.0 mm and about 2.5 mm, or between about 1.0 mm and about 2.0 mm, or between about 1.5 mm and about 2.5 mm), thus leaving behind no permanent scars. The method can also include inserting the control portion into the patient through the plurality of control incisions, and extending a distal portion of the control portion through the tool incision and out of the patient. Additionally, the method can include removably securing the control portion to the tool portion. After securing the control portion and the tool portion, the entire instrument can be retracted through the tool incision and into the patient.

In the above-mentioned method, the surgical instrument can also include a locking assembly having a frame member surrounded by a release ring having at least one cam surface. In certain aspects, the method can include rotating the release ring such that the cam surface secures at least one of the plurality of control rods to at least one of the plurality of tool rods.

In any of the above-mentioned methods, the method can further include securing a central shaft of the tool portion to a collapsible mandrel of the tool portion. In certain aspects, rotation of the central shaft rotates the plurality of tool cables and moves the collapsible mandrel between a collapsed configuration and an elongated configuration.

The surgical instruments and methods discussed herein can be used in robotic applications, including but not limited to scarless procedures. In the robotic application, the operator can indirectly manipulate the tool using computer or mechanically-assisted systems, whether or not the operator is present in the same room as the patient.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 2A illustrates a proximal portion of the control portion without an adapter.

FIGS. 4A-4E illustrate steps of an exemplary method for connecting the control portion and the tool portion.

DETAILED DESCRIPTION

During open surgery, surgeons make large incisions that allow them to insert both hands into the abdominal cavity and/or tools held in both hands. This traditional open surgery requires large incisions that can accommodate retractors and tools inserted into the abdominal cavity. However, these large incisions can slow down the recovery process, leave behind large scars, and cause increased amounts of pain during the recovery period.

During the 1990s, robotic surgery was applied to many disease processes. Robotic surgical systems generally include a console in communication with a patient-side cart. The patient-side cart can include a multiple number of robotic arms connected to one or more interchangeable surgical instruments. The robotic systems translate surgeon hand movements at the console into corresponding micro-movements of the surgical instruments and filter out hand tremors. Traditionally, the surgical instruments are inserted through multiple incisions in the patient's body that are each about 1 to 2 cm long. Although these incisions are generally smaller than traditional open surgery incisions, robotic surgery still leaves behind permanent scars. Accordingly, there is a need to produce robotic surgical instruments that leave behind no scars. To do so, the surgical instruments must be capable of insertion through incisions having an outer diameter of less than or equal to about 2.5 mm, while still providing the surgical instruments with sufficient rigidity for insertion and a full range of movement (e.g., in and out, shaft rotation, up-down shaft movement, left-right shaft movement, up-down tool movement, left-right tool movement, and grip for scissors and forceps).

Surgical Instrument

Figure 1:
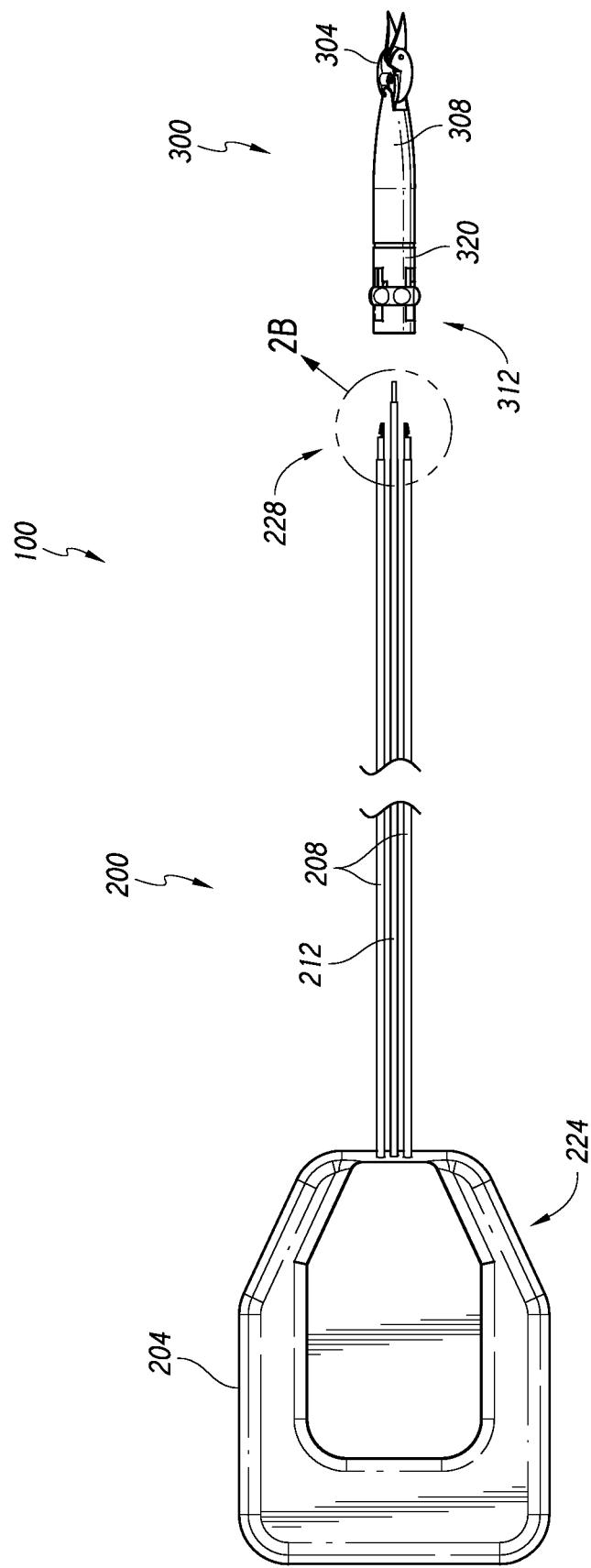
FIG. 1 illustrates a left-side view of a disassembled surgical instrument having a control portion and a tool portion.

FIG. 1 illustrates a disassembled view of an exemplary instrument 100 for use in surgery, including but not limited to robotic surgery. The surgical instrument 100 can include a control portion 200 that can removably engage a tool portion 300. If the instrument 100 is being used for robotic surgery, the control portion 200 can include an adapter 204 that can be secured to the robotic arm. The adapter 204 can provide an electrical and/or mechanical interface between the robotic arm and the surgical instrument 100. For example, the robotic arm can include one or more wheels that correspond to wheels (not shown) on the adapter 204. These wheels can transmit mechanical force via a plurality of control cables 240 (see FIG. 2A) that can be used to articulate a working end 304 of the surgical instrument. As described in further detail below, each of the plurality of control cables 240 can be secured to a control rod 232 (see FIG. 2A). Each control rod 232 can have a diameter that is greater than a diameter of each control cable and sufficiently large, and thus sufficiently rigid, to facilitate insertion of the control portion 200 through the skin of the patient. At least one of the control rods 232 (e.g., one, two, three, or more) can extend through each tubular shaft portion 208 (see FIGS. 2A and 2B). Each of the control rods 232 can removably engage a tool rod 352 (see FIGS. 4A-4E). Further, each of the tool rods 352 can be secured to a tool cable 364 (see FIG. 3C). Through these connections, the adapter 204 can transmit mechanical force from the robotic arm to the control cables 240 and corresponding tool cables 364, which can articulate the working end 304 (e.g., by using a number of pulleys 368).

With conventional robotic surgical instruments, all of the cables are delivered through a single shaft, thus increasing the diameter of the shaft and the length of the skin incision necessary to accommodate the surgical instrument. Advantageously, providing a separate shaft for each cable or subset of cables allows the surgical instrument 100 to be introduced through multiple, smaller incisions that leave behind no permanent scars. Further, each shaft provides sufficient rigidity to deliver the instrument through the incisions.

Figure 2B:
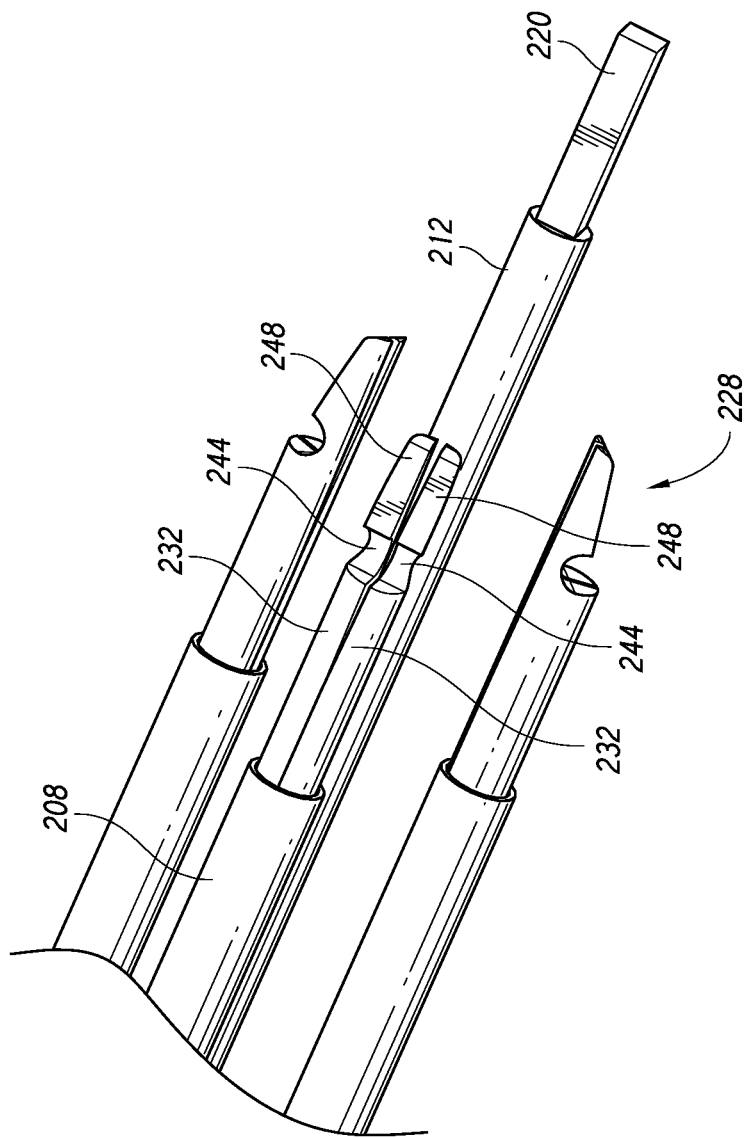
FIG. 2B illustrates a distal portion of the control portion shown in FIG. 1 and taken along line 2B.
Figure 2C:
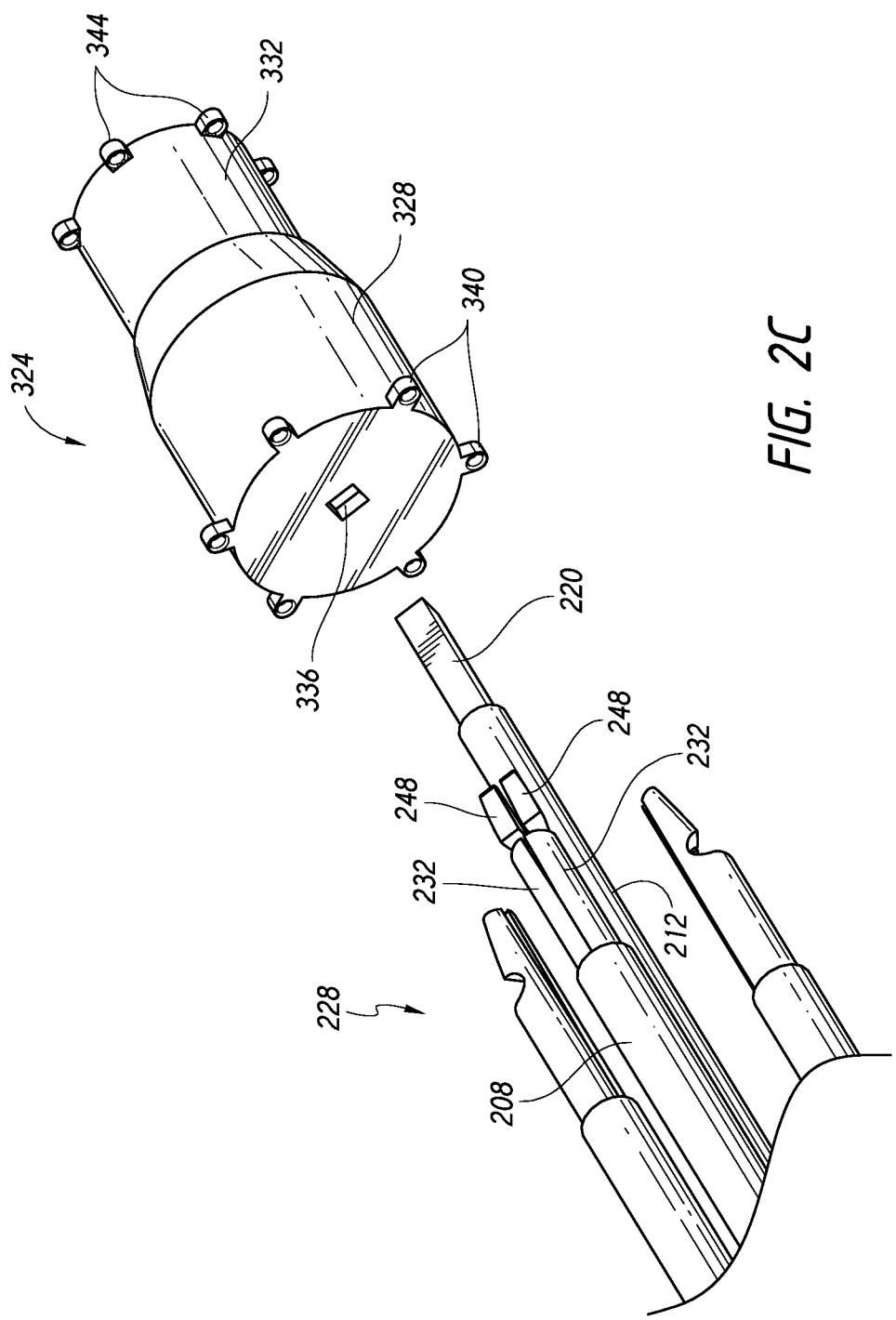
FIG. 2C illustrates the distal portion of the control portion and a collapsible mandrel of the tool portion.

As shown in FIG. 1, the control portion 200 can have a proximal portion 224 including the adapter 204. A plurality of shaft portions 208 can extend from the adapter 204 (e.g., two shaft portions, three shaft portions, four shaft portions, five shaft portions, six shaft portions, or more). The shaft portions 208 can be equally spaced apart and circumferentially disposed around a central shaft 212. For example, as shown in FIGS. 2A-2C, the control portion 200 can include three shaft portions 208 circumferentially disposed around the central shaft 212. The shaft portions 208 enable in and out movement, up-down shaft movement, left-right shaft movement, up-down tool movement, left-right tool movement, and/or tool operation, while the central shaft 212 enables tool rotation and/or electrocautery. Further, each of the shaft portions 208 and the central shaft 212 can have an outer diameter of less than or equal to about 2.5 mm (e.g., less than or equal to about: 2.0 mm, 1.5 mm, 1.0 mm, or between about 1.0 mm and about 2.5 mm, or between about 1.0 mm and about 2.0 mm, or between about 1.5 mm and about 2.5 mm), so the control portion 200 can be inserted into the patient through a number of incisions each having a length of less than or equal to about 2.5 mm.

Each of these shaft portions 208 can be inserted without a port, so that movement of the shaft portions 208 allows the control rods 232 to slide through the skin without causing injury to adjacent structures. Port-less entry has been shown in animal studies to cause no increased scarring (See Cosmetic Impact of Needlescopic and Portless Needlescopic Instruments Abstract, published in November 2011 at the World Congress of Endourology, which is hereby incorporated by reference in its entirety). Alternatively, the shaft portions 208 can be inserted through a special port that allows smooth movement of each of the shaft portions 208. The port can be positioned on a surface of the skin and link the shaft portions 208, while providing conduits for each of the shaft portions 208 to slide in and out more smoothly without applying friction to the adjacent structures.

As described above, one or more wheels in the adapter can interface with and drive a plurality of control cables 240. Each of the cables 240 can be secured to a control rod 232 (see FIG. 2A). For example, each of the cables 240 can be secured to a proximal portion of a control rod 232 using a control connector 236. The control rods 232 alone or in combination with the shaft portions 208 provide sufficient rigidity for insertion into the patient, while still minimizing the size of the incisions necessary to accommodate the control portion 200. As another example, each cable 240 can form an integral structure with the control rod 232, with each control rod 240 having a diameter that is greater than a diameter of the cable 240.

The shape of the control rods 232 can depend on the number of control rods 232 extending through each shaft portion 208. A subset of the control rods 232 (e.g., two, three, four, or otherwise) can be shaped to collectively extend through a tubular shaft portion 208. For example, as shown in FIG. 2A, two control rods 232 can extend through each shaft portion 208. If two control rods 323 extend through a shaft portion 208, each control rod 232 can have a semi-circular cross-section. Extending multiple control rods 232 through a single shaft portion 208 can reduce the total number of necessary incisions, while still accommodating each of cables (or other drivers) in the robotic arm (e.g., the number of shaft portions, and thus incisions, relative to the number of robotic arm cables (or drivers) can be: one-half, one-third, one-fourth, or otherwise).

Additionally, the control connectors 236 can be shaped to accommodate the shape of the control rods 232. For example, when the control rods 232 have a semi-circular cross-section, the control connectors 236 can include a semi-circular passageway (e.g., channel, groove, indentation, opening, or likewise) to accommodate the control rod 232.

FIG. 2B illustrates the distal portion 228 of the control portion 200. A distal portion of each of the control rods 232 can engage a proximal portion of each tool rod 352 (e.g., using hooks, screw threads, snap fits, or other engagements). For example, the hooked portions 244 of the control rods 232 can removably engage the hooked portions 354 of the tool rods 352. Additionally, the distal portion of each control rod 232 can include an insertion portion 248. Each insertion portion 248 can narrow to a sharpened tip to facilitate insertion through the skin. Alternatively, these insertion portions can be smoothly tapered, but not sharp, to allow insertion through the ports as discussed previously.

Further, as shown in FIG. 2C, the tool portion 300 can optionally include a collapsible mandrel 324. The central shaft 212 can include a distal portion 220 shaped for insertion into a lumen 336 of the collapsible mandrel 324 of the tool portion 300. For example, the lumen 336 can have a square-shaped cross-section to receive the square-shaped distal portion 220 of the central shaft 212. As described in further detail below, rotation of the central shaft 212 can cause the collapsible mandrel 324 to move between an elongated configuration and a collapsed configuration.

The number of shaft portions 208 can vary depending on the number of control rods 232 extending through each shaft portion 208. Further, the number of control rods 232 can vary depending on the number of control cables 240. For example, the surgical instrument 100 can have the same number of control rods 232 and control cables 240. As shown in FIG. 2A, the surgical instrument 100 includes six control cables 240 and six control rods 232 to provide a full range of movement. Two control rods 232 can extend through each shaft portion 208, thus the illustrated surgical instrument 100 includes three shaft portions 208, although other ratios between control rods and shaft portions can be imagined as described above.

Although not shown, the control portion 200 can include a support member (e.g., a ring, triangle, or other suitable shape) surrounding a distal portion of the shaft portions 208 to maintain the alignment of the shaft portions 208. For example, the support member can include a number of openings for each of the shaft portions 208 and can slidably move along the shaft portions 208 when the control portion 200 is inserted into the patient.

Figure 3A:
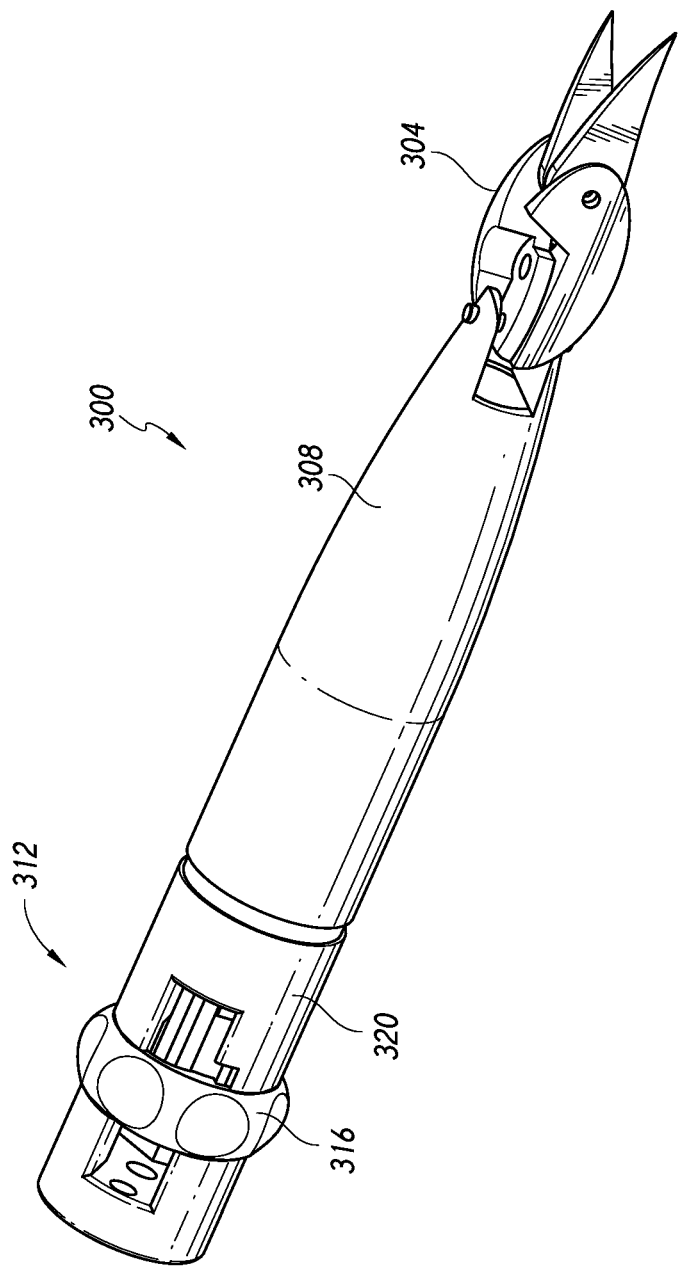
FIG. 3A illustrates a perspective view of the tool portion.
Figure 3B:
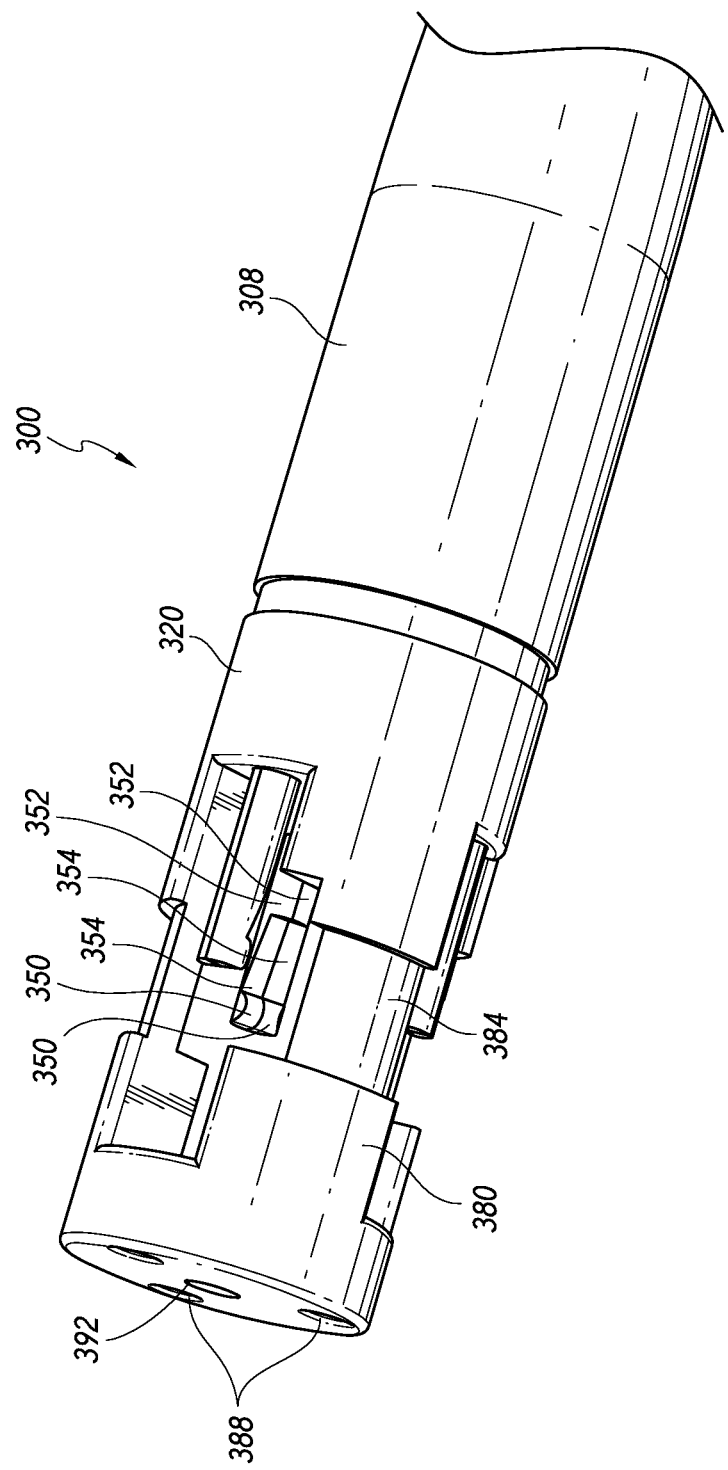
FIG. 3B illustrates a perspective view of a proximal portion of the tool portion without a release ring.

FIG. 3A illustrates an enlarged view of the tool portion 300 shown in FIG. 1. The tool portion 300 can include a working end 304 (e.g., scissors, forceps, electrocautery hook, needle drive, or otherwise). The tool portion 300 can also include an outer cover 308 that can surround the collapsible mandrel 324 and tool cables 364 (see FIG. 3C). Proximal to the outer cover 308, the tool portion 300 can include a locking assembly 312 to secure the control rods 232 to the tool rods 352. As shown in FIG. 3B, the locking assembly 312 can have a frame member 320 surrounded by a release ring 316. The frame member 320 can include a number of struts 380. Each of the struts 380 can define a recessed portion 384 for receiving the release ring 316 that can rotate between a first position and a second position. As shown in FIG. 4E, the release ring 316 can include at least one cam surface 372 on an inner surface of the release ring 316. When the release ring 316 is in the first position, the cam surface 372 secures the connection between the control rods 232 and the tool rods 352. When the release ring 316 is moved to the second position, the cam surface 372 does not extend across the control rods 232 or the tool rods 352, thereby releasing the connection.

Additionally, as shown in FIG. 3B, a proximal end 348 of the frame member 320 can include a number of openings 388 for receiving the shaft portions 208, and a central opening 392 for receiving the central shaft 212. These openings 388, 392 can help maintain the alignment of the shaft portions 208 and the central shaft 212.

As described above, the tool portion 300 can include a number of tool rods 352. The number of tool rods 352 can be equal to the number of control rods 232. A proximal portion of each of the tool rods 352 can interface with a distal portion 350 of each of the control rods 232 (e.g., using hooks, screw threads, snap-fits, or otherwise). For example, as shown in FIG. 3B, the hooked portions 354 of the tool rods 352 can be shaped to engage the hooked portions 244 of the control rods 232.

FIGS. 4A-4E illustrate a method of securing the tool portion 300 to the control portion 200. As shown in FIGS.

Figure 4C:
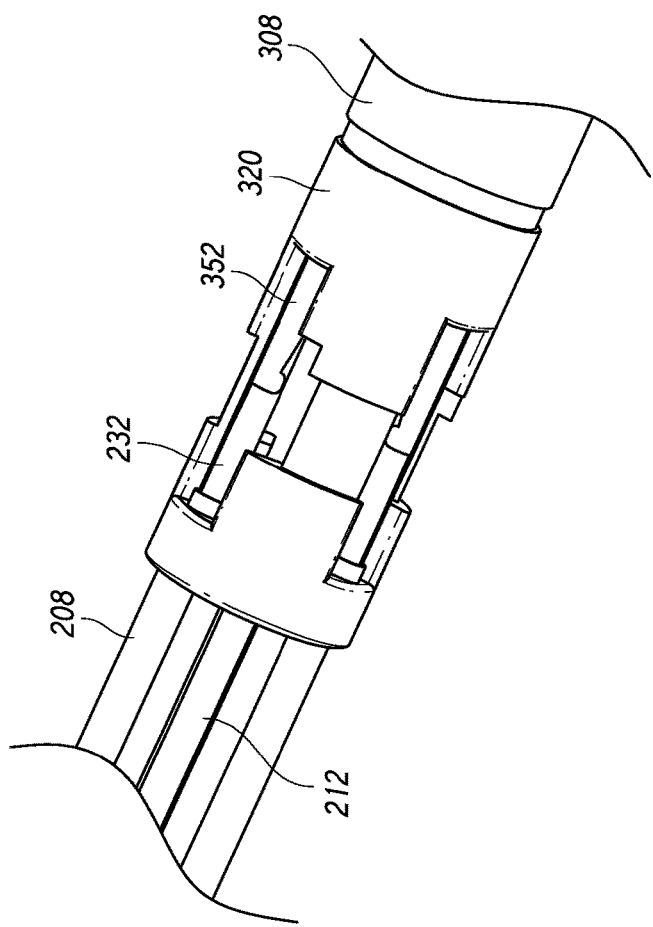
Figure 4D:
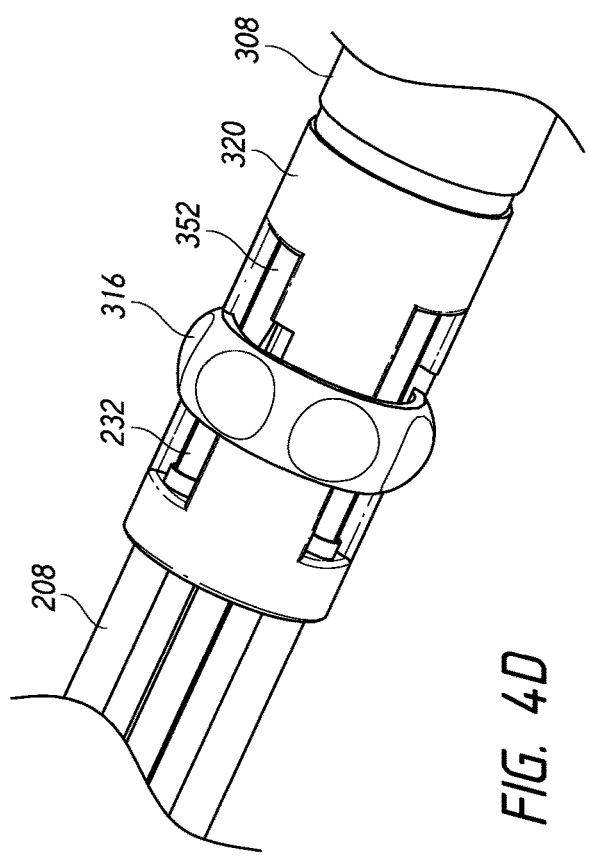

4A and 4B, the distal portion 228 of the control portion 200 can be introduced into the frame member 320 until each control rod 232 engages a corresponding tool rod 352, e.g., by connecting control hooks 244 and tool hooks 354 (see FIG. 4C). Thereafter, the release ring 316 can be rotated until the cam surface 372 secures the connection between the control rods 232 and the tool rods 352 (see FIG. 4E). To release the connection, the release ring 316 can be rotated in the opposite direction (see FIG. 4D) and the tool portion 300 can be disconnected from the control portion 200.

Figure 3C:
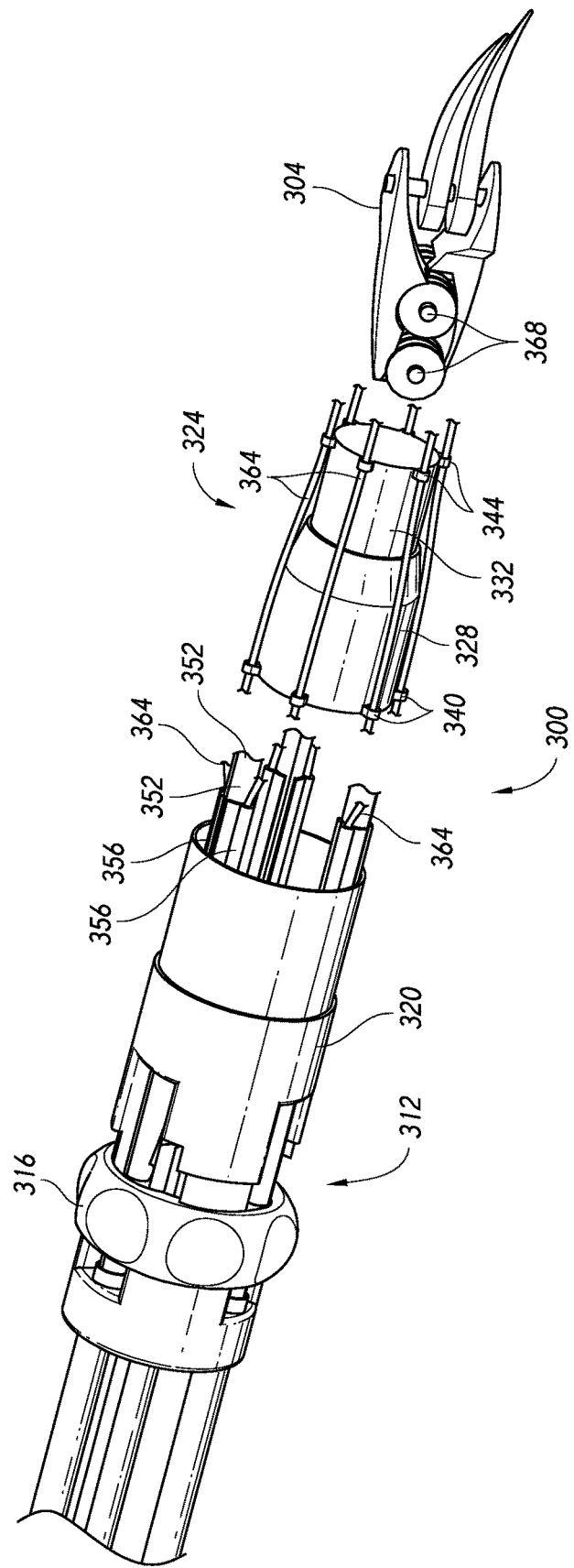
FIG. 3C illustrates a partial exploded view of the tool portion.

As shown in FIG. 3C, a control cable 364 can extend from a distal portion of each tool rod 352, across the collapsible mandrel 324, to the working end 304. A tool connector 356 can secure each tool rod 352 to a tool cable 364. The tool connectors 356 can be shaped similarly to the control connectors 236 described above. When the surgical instrument 100 is fully assembled, each tool cable 364 can be connected to one of the control cables 240 via the control rods 232, thus enabling the operator to control the tool portion 300 through the control portion 200. Alternatively, each cable 364 can form an integral structure with the tool rod 352, with each tool rod 352 having a diameter that is greater than a diameter of the cable 364.

The collapsible mandrel 324 can include an outer member 328 movable relative to an inner member 332 along a helical cam path 376 on the surface of the inner member 332. Each of the tool cables 364 can interface with a proximal end of the collapsible mandrel 324 and a distal end of the collapsible mandrel 324. As shown in FIG. 3C, the collapsible mandrel 324 can include a number of openings 340, 344 at each of the proximal and distal ends of the 324 mandrel for receiving each of the tool cables 364. These openings 340, 344 maintain the spacing between the tool cables 364 to facilitate control of the working end 304.

Figures 5A, 5B:
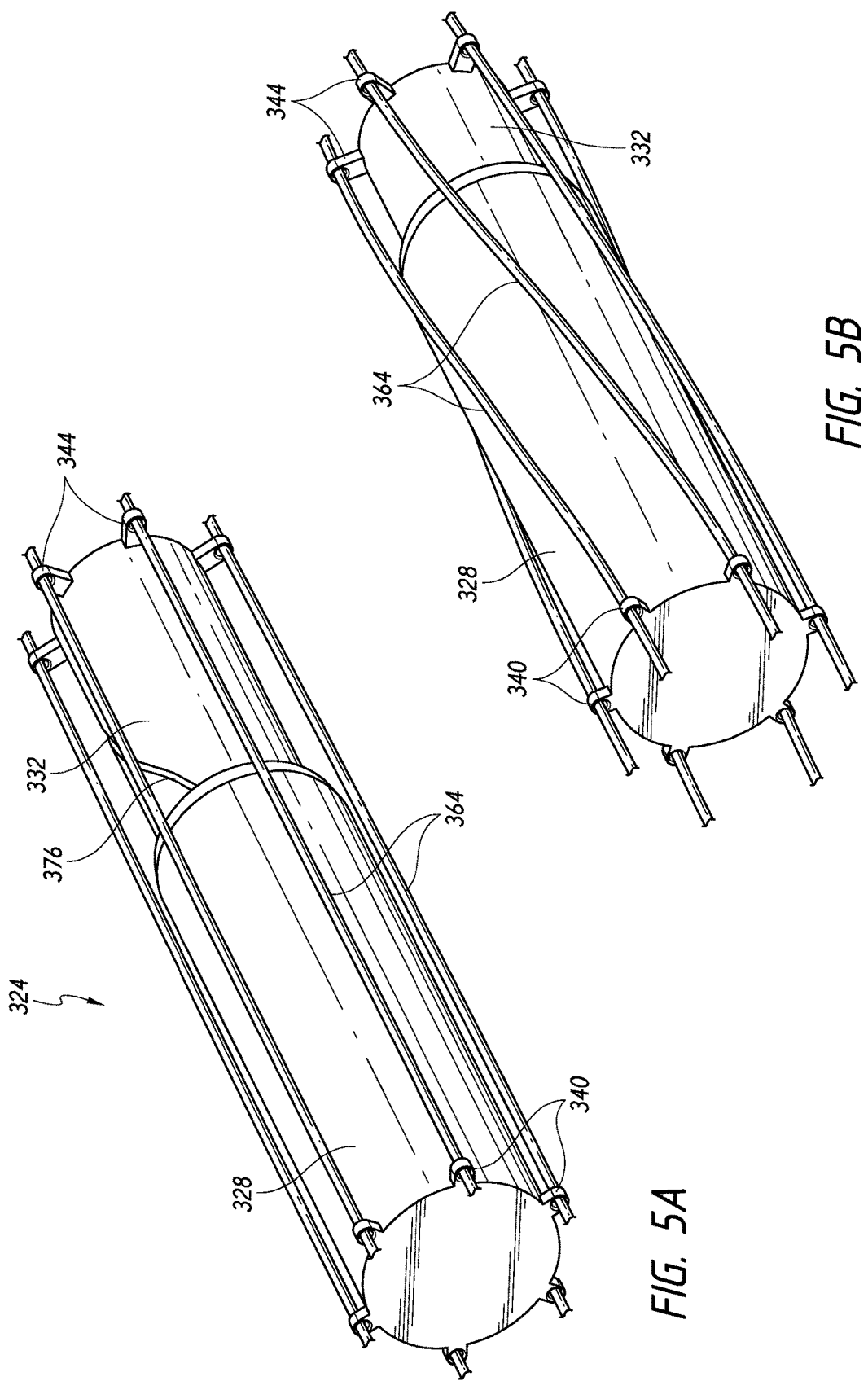
FIG. 5A illustrates a collapsible mandrel in an elongated configuration.
FIG. 5B illustrates the collapsible mandrel shown in FIG. 5A in a collapsed configuration.

As described above, the central shaft 212 can drive rotation of the working end 304. However, when the central shaft 212 rotates, the length of the tool cables 364 can change as shown in FIGS. 5A and 5B. If the tool cables 364 are not reasonably taut, the cables 364 can intertwine and/or affect operation of the working end 304. As such, it can be desirable to provide a collapsible mandrel 324 that can adjust based on the length of the tool cables 364. For example, when the tool cables 364 are pulled taut, the collapsible mandrel 324 can be in an elongated configuration (see FIG. 5A). As the central shaft 212 rotates, the central shaft 212 can drive the outer member 328 relative to the inner member 332 to shorten the length of the collapsible mandrel 324 based on the shortened length of the tool cables 364. The collapsible mandrel 324 permits the working end 304 to be rotated by 180 degrees in both a clockwise and counterclockwise direction, while still keeping the tool cables 364 reasonably taut and maintaining similar spacing between the tool cables 364.

Method of Use

As described above, the surgical instrument 100 described herein can be used to perform a surgical procedure, which can include a robotic procedure and/or a procedure that does not leave behind scars. After insufflation, a plurality of control incisions can be formed for each of the shaft portions 208 and the central shaft 212 (if present) (e.g., two, three, four, or more incisions). Each of the control incisions can have a length of less than or equal to about 2.5 mm (e.g., less than or equal to about: 2.0 mm, 1.5 mm, 1.0 mm, or between about 1.0 mm and about 2.5 mm, or between about 1.0 mm and about 2.0 mm, or between about 1.5 mm and about 2.5 mm). An incision having a length of less than or equal to about 2.5 mm will not leak insufflation and will not create any permanent scars. The control incisions can be formed using a scalpel or other sharpened tip, or using the insertion portions 248 of the control portion 200 (see FIG. 2B). The insertion portions 248 can each have a sharpened tip to create each of the control incisions.

Optionally, a support structure can surround the shaft portions 208 and the central shaft 212 to maintain the alignment of the shaft portions 208 and position of the shaft positions 208 relative to each other and the central shaft 212. For example, the support structure can be ring-shaped and movable along the shaft portions 208 alone or in combination with the central shaft 212. Initially, the support structure can be positioned around a distal portion of the shaft portions 208. As the control portion 200 is inserted into the patient, the support structure remains positioned against the patient's body and the shaft portions 208 move relative to the support structure.

After the distal portion 228 of the control portion 200 has been inserted into the patient, the distal portion 228 can extend out of the patient through a tool incision created in the umbilicus. The tool incision can be larger than 2.5 mm; however, any scar left behind will be hidden. When the distal portion 228 is outside of the patient, the tool portion 300 can be secured to the control portion 200 using, for example, the method shown in FIGS. 4A-4E. As shown in FIGS. 4A and 4B, a distal portion 228 of the control portion 200 can be introduced into the frame member 320 until the control rods 232 engage the tool rods 352 (see FIG. 4C). Thereafter, the release ring 316 can be rotated until the cam surface 372 secures the connection between the control rods 232 and the tool rods 352 (see FIG. 4E). Once the control portion 200 and the tool portion 300 are connected, the surgical instrument 100 can be withdrawn through the tool incision and back into the patient for the procedure. When the surgical instrument 100 is fully assembled, the operator imparts movement to the tool portion 300 through the control portion 200. For example, movement of the control cables 240 can move the control rods 232, which in turn move the tool rods 352. Movement of the tool rods 352 causes the tool cables 364 to move, which control the working end 304. If the surgical instrument 100 includes the collapsible mandrel 324, movement of the tool cables 364 causes the collapsible mandrel 324 to move between an elongated configuration and a collapsed configuration to keep the cables 364 taut, for proper operation of the working end 304.

To exchange the tool portion 300, the tool portion 300 can extend back out of the patient through the tool incision. To release the connection between the control portion 200 and the tool portion, the release ring 316 can be rotated in the opposite direction (see FIG. 4D) and the tool portion 300 can be disconnected from the control portion 200. Further information regarding the exchange of tool portions in the context of non-robotic surgical devices can be found in U.S. Pat. No. 8,225,798, filed May 18, 2010, titled "Method and devices for performing minimally invasive surgery," or U.S. Publication No. 2014/0309677, filed Apr. 10, 2014, titled "MINIMALLY INVASIVE SURGICAL DEVICES AND METHODS," both of which are hereby incorporated by reference in their entirety.

Terminology

"Scarless" is a broad term that is to be given its ordinary and customary meaning to a person of ordinary skill in the art (i.e., it is not to be limited to a special or customized meaning) and includes, without limitation, scars that cannot be detected by an experienced surgeon at a distance of five feet from the patient, at least four weeks after the surgery.

"Robotic surgery" is a broad term that is to be given its ordinary and customary meaning to a person of ordinary skill in the art (i.e., it is not to be limited to a special or customized meaning) and includes, without limitation, the use of computer-assisted systems to aid a surgical procedure.

"Control portion" is a broad term that is to be given its ordinary and customary meaning to a person of ordinary skill in the art (i.e., it is not to be limited to a special or customized meaning) and includes, without limitation, a portion of a surgical instrument configured to impart movement of a surgical system to a tool portion.

"Tool portion" is a broad term that is to be given its ordinary and customary meaning to a person of ordinary skill in the art (i.e., it is not to be limited to a special or customized meaning) and includes, without limitation, a portion of a surgical instrument configured to move in response to movement of a control portion (e.g., in and out, shaft rotation, up-down shaft movement, left-right shaft movement, up-down tool movement, left-right tool movement, and/or operate a function, such as gripping, cutting, or otherwise).

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount as the context may dictate.

Although certain embodiments and examples have been described herein, it will be understood by those skilled in the art that many aspects of the surgical instruments shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "forming a plurality of control incisions" include "instructing formation of a plurality of control incisions."

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 2.5 mm" includes "2.5 mm."

What is claimed is:

1. A surgical instrument comprising:
    a control portion comprising a plurality of tubular shaft portions and a plurality of control rods, each of the plurality of tubular shaft portions having a diameter of less than or equal to about 2.5 mm, each control rod extending through one of the plurality of shaft portions; and
    a tool portion having a plurality of tool rods and a plurality of tool cables, the plurality of tool rods being positioned circumferentially from each other around a central axis of the tool portion, each of the plurality of tool cables connected to one of the plurality of control rods, each of the tool rods being removably connected to one of the plurality of control rods.

2. The surgical instrument of claim 1, further comprising a plurality of tool connectors, wherein each of the plurality of tool cables is connected to one of the plurality of tool rods by one of the tool connectors.

3. The surgical instrument of claim 1, wherein the plurality of tool cables are configured to drive a plurality of pulleys in a working end.

4. The surgical instrument of claim 1, wherein the control portion further comprises a central shaft surrounded by the plurality of tubular shaft portions.

5. The surgical instrument of claim 1, wherein a distal portion of each of the control rods comprises a hook.

6. The surgical instrument of claim 1, wherein a proximal portion of each of the plurality of the tool rods comprises a hook.

7. The surgical instrument of claim 1, wherein at least two of the plurality of control rods extend through each of the plurality of shaft portions.

8. The surgical instrument of claim 1, wherein the tool portion further comprises a locking assembly for securing the plurality of the control rods with the plurality of tool rods.

9. The surgical instrument of claim 8, wherein the locking assembly comprises a frame member and a release ring surrounding the frame member, the release ring having at least one cam surface that secures at least one of the plurality of control rods to at least one of the plurality of tool rods.

10. The surgical instrument of claim 1, wherein the control portion further comprises an adapter configured to engage a robotic arm.

11. The surgical instrument of claim 10, wherein the adapter further comprises a plurality of control cables, each of the plurality of control cables secured to one of the plurality of control rods.

12. The surgical instrument of claim 11, further comprising a plurality of control connectors, wherein each of the plurality of control cables is secured to one of the plurality of control rods by one of the control connectors.

13. The surgical instrument of claim 1, further comprising a support structure surrounding the plurality of shaft portions to maintain alignment of the plurality of shaft portions.

14. The surgical instrument of claim 1, wherein two control rods extend through one of the plurality of shaft portions.

15. A method of using a surgical instrument, the method comprising:
   forming a plurality of control incisions on a patient, each of the control incisions having a length of less than or equal to about 2.5 mm;
   inserting a control portion through the plurality of control incisions, the control portion comprising a plurality of tubular shaft portions and a plurality of control rods, the plurality of tubular shaft portions having a diameter of less than or equal to about 2.5 mm, each control rod extending through one of the plurality of shaft portions;
   forming a tool incision on the patient; and
   extending a distal portion of the control portion through the tool incision and out of the patient;
   securing the control portion to a tool portion, the tool portion comprising a plurality of tool rods and a plurality of tool cables, the plurality of tool rods being positioned circumferentially from each other around a central axis of the tool portion, each of the plurality of tool cables connected to one of the plurality of control rods, each of the tool rods being removably connected to one of the plurality of control rods; and
   retracting the distal portion of the control portion and the tool portion through the tool incision and into the patient.

16. The method of claim 15, further comprising securing an adapter of the control portion to a robotic arm.

17. The method of claim 15, further comprising locking a locking assembly having a frame member and a release ring surrounding the frame member, the release ring having at least one cam surface.

18. The method of claim 17, wherein locking the locking assembly comprises rotating the release ring such that the at least one cam surface secures at least one of the plurality of control rods to at least one of the plurality of tool rods.

19. The method of claim 15, wherein two control rods extend through one of the plurality of shaft portions.

20. A method of assembling a surgical tool, the method comprising:
   securing a control portion and a tool portion, the control portion comprising a plurality of tubular shaft portions having a diameter of less than or equal to about 2.5 mm, each control rod extending through one of the plurality of shaft portions, the tool portion comprising a plurality of tool rods and a plurality of tool cables, each of the plurality of tool cables connected to one of the plurality of control rods, each of the tool rods being removably connected to one of the plurality of control rods, the tool portion further comprising a locking assembly having a frame member and a release ring surrounding the frame member, the release ring having at least one cam surface; and
   rotating the release ring so that the at least one cam surface secures at least one of the plurality of control rods to at least one of the plurality of tool rods.

21. The method of claim 20, further comprising securing an adapter of the control portion to a robotic arm.

22. The method of claim 20, wherein two control rods extend through one of the plurality of shaft portions.

* * * * *